United States Patent [19]

Akiyama

[11] Patent Number: 4,575,252
[45] Date of Patent: Mar. 11, 1986

[54] APPARATUS FOR MEASURING ABSOLUTE REFLECTANCE

[75] Inventor: Osamu Akiyama, Kyoto, Japan

[73] Assignee: Shimadzu Corporation, Kyoto, Japan

[21] Appl. No.: 542,150

[22] Filed: Oct. 14, 1983

[30] Foreign Application Priority Data

Oct. 29, 1982 [JP] Japan ................................. 57-191306

[51] Int. Cl.⁴ ............................................. G01N 21/47
[52] U.S. Cl. .................................... 356/446; 250/228; 356/236
[58] Field of Search ............... 356/445, 446, 244, 319, 356/321, 405, 406, 243, 236, 73, 447–448; 250/228

[56] References Cited

U.S. PATENT DOCUMENTS

| | | | |
|---|---|---|---|
| 1,964,365 | 6/1934 | Razek et al. | 356/319 |
| 3,327,583 | 6/1967 | Vanderschmidt et al. | 356/446 X |
| 3,502,890 | 3/1970 | Hedelman | 250/228 |
| 3,874,799 | 4/1975 | Isaacs et al. | 356/405 X |
| 4,093,991 | 6/1978 | Christie, Jr. et al. | 364/498 X |

*Primary Examiner*—Vincent P. McGraw
*Assistant Examiner*—Robert D. V. Thompson, III
*Attorney, Agent, or Firm*—Fidelman, Wolffe & Waldron

[57] ABSTRACT

Apparatus for measuring the absolute reflectance of a sample, which comprises an integrating sphere provided with four windows the centers of which lie in a plane including the center of the integrating sphere. A first one of the four windows has its center coinciding with a diametrical line of the integrating sphere included in the plane while a second and a third window are arranged symmetrically with respect to the diametrical line, with a sample set in the fourth window so as to face inwardly of the integrating sphere. A light source is so arranged as to introduce a beam of light into the integrating sphere and a light measuring device is so arranged as to receive the light emerging from the integrating sphere. The integrating sphere is rotatable for 180° about an axis coinciding with the above-mentioned diametrical line so that the integrating sphere selectively takes two positions thereby to change the operative positions of the second and third windows relative to the light source or the light measuring device. The data measured at each of the two positions of the integrating sphere are processed so as to obtain the absolute reflectance of the sample. The positions of the light source and the light measuring device relative to the windows of the integrating sphere may be exchanged to obtain a different type of absolute reflectance.

6 Claims, 10 Drawing Figures

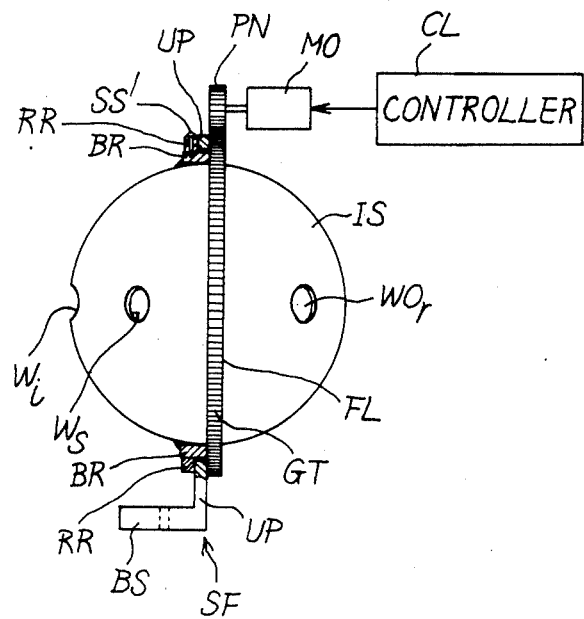
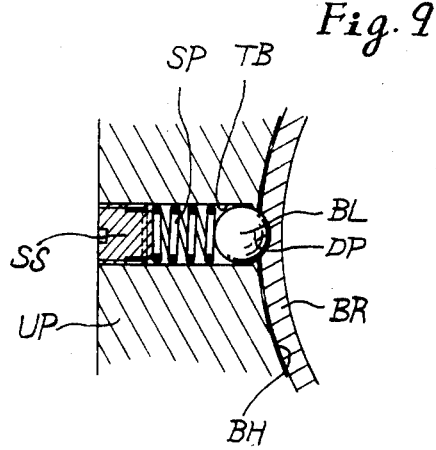

APPARATUS FOR MEASURING ABSOLUTE REFLECTANCE

BACKGROUND OF THE INVENTION

This invention relates to an apparatus for measuring the absolute reflectance of a sample, which employs an integrating sphere.

There are two methods of measuring the reflectance of a sample. One is to measure the relative reflectance of a given sample material to be measured, with the known reflectance of a standard or reference material being taken as 100%, and the other is to measure the true or absolute reflectance of a sample material.

Usually, the relative reflectance of a given sample material (to be referred to as a sample) is first measured and the measured value is multiplied by the absolute reflectance of a reference material (to be referred to as a reference) so as to obtain the absolute reflectance of the sample under measurement. However, the absolute reflectance of the reference is given merely as one of various data and if the reflectance changes as time passes, such changes are not known to the person who is conducting the measurement, so that it is impossible to measure the absolute reflectance of the sample.

The principle of measuring absolute reflectance is simple, but great difficulties are encountered in putting it into practice. One known method of measuring the absolute reflectance of a sample employs an integrating sphere. The method is somewhat complicated in theory but relatively easy to put into practice. In the method which employs an integrating sphere, however, since it is necessary to move the photodetector or the optical path relative to the integrating sphere, a complicated mechanism is required for effecting the relative movement so that the whole structure of the apparatus becomes of a large size. Although the apparatus may be used in a laboratory, it is not suitable for practical use, and it is even more difficult to design the apparatus as an adaptor for ready use in a spectrophotometer.

The principle of measurement of absolute reflectance will first be explained with reference to FIG. 1. There is shown an integrating sphere IS provided with an inlet window WI, through which a light beam Li from a monochromator MC is introduced into the integrating sphere so as to directly illuminate a region Wa on the inner surface of the integrating sphere. The integrating sphere is also formed with a sample window Ws and a pair of outlet windows WOs and WOr. A sample SM is set in the sample window Ws so as to face inwardly of the integrating sphere, and the sample beam Ls comes out of the window WOs and the reference beam Lr, out of the window WOr.

Inside the integrating sphere there is provided a screen SC so arranged as to prevent the light which enters the integrating sphere through the window WI and is reflected directly by the region Wa, that is, the light of the first reflection on the region Wa from striking the sample set in the window Ws. The screen SC is provided at such a position that it cannot be seen through the light measuring system at either one of the outlet windows WOs and WOr. In FIG. 1, for example, the reference light beam Lr is being measured, with a lens LN forming an image of a region Wr on the inner surface of the integrating sphere IS diametrically opposite the outlet window WOr on an aperture AP disposed in front of a photodetector PD. The region Wr is conjugate with the aperture AP and the screen SC is completely out of the optical path of the light Lr which forms the image of the region Wr on the aperture AP. The inner surface of the integrating sphere IS has a uniform, high reflectance r. The screen SC is so painted that its reflectance also is r.

Let the amount of the light Li that enters the integrating sphere IS be expressed by P; the area of the inner surface of the sphere, by S; the area of the window WOr and that of the window WOs, both by b; the area of the sample window Ws and that of the region Wr, both by a; the reflectance of a sample, by r'; and $a/S=k_1$ and $b/S=k_2$.

The above-mentioned reflectances r and r' are absolute reflectances.

With a sample SM to be measured having been set in the sample window Ws as shown in FIG. 1, the light Lr emerging out of the integrating sphere IS through the outlet window WOr and the lens LN is measured. The light Li entering the integrating sphere is reflected by the region Wa uniformly in all directions, and the total amount of the reflected light is P·r, of which the amount of the light that hits the region Wr is $P \cdot r \cdot a/S = P \cdot r \cdot k_1$, and the amount $Ir_1$ of the light that is reflected by the region Wr to emerge out of the outlet window WOr is given as $$Ir_1 = P \cdot r \cdot k_1 \cdot r \cdot k_2. \tag{1}$$

On the other hand, the amount of the light that is reflected by the region Wa in the directions other than toward the region Wr is $P \cdot r(1-k_1)$. The light reflected by the region Wa in the other directions is reflected for the first time by the inner surface of the integrating sphere and the total amount of the reflected light is $P \cdot r(1-k_1)r$, of which the amount of the light that hits the region Wr is $P \cdot r(1-k_1)r \cdot k_1$, and the amount $Ir_2$ of the light that is reflected by the region Wr to emerge out of the outlet window WOr is given as $$Ir_2 = P \cdot r(1-k_1)r \cdot k_1 \cdot r \cdot k_2. \tag{2}$$

The light reflected for the first time by the inner surface of the integrating sphere IS is again reflected by the inner surface of the integrating sphere. The amount $Ir_3$ of the light reflected for the second time to hit the region Wr to be reflected thereby to merge out of the window WOr is given as $$Ir_3 = P \cdot r(1-k_1)r(1-k_1)r \cdot k_1 \cdot r \cdot k_2. \tag{3}$$

In a similar manner reflection of the light is repeated, so that the total amount Ir of the light taken out of the window WOr is the sum of the amounts $Ir_1$, $Ir_2$, $Ir_3$, ... and given as $$\begin{aligned}Ir &= P \cdot r^2 \cdot k_1 \cdot k_2[1 + r(1-k_1) + r^2(1-k_1)^2 + \ldots] \\ &= P \cdot r^2 \cdot k_1 \cdot k_2 \frac{1}{1 - r(1-k_1)}.\end{aligned} \tag{4}$$

Then, the light measuring device comprising the lens LN, the aperture AP and the photodetector PD is transferred to the other outlet window WOs so that the sample SM is aligned with the window WOs and the light measuring device.

At this time in a manner similar to the above-mentioned manner in which the amount Ir is obtained, the amount Is of the light that emerges out of the sample light outlet window WOs is given as $$Is = P \cdot r^2 \cdot k_1 \cdot r' k_2 \frac{1}{1 - r'(1 - k_1)}. \quad (5)$$

It should be noted here that the light entering the integrating sphere IS and being reflected for the first time by the region Wa is intercepted by the screen SC so that it does not impinge on the sample SM. Therefore, the light that impinges on the sample for the first time is the light reflected by the region Wa and then reflected by the inner surface of the integrating sphere, and the amount of this light is given as $P \cdot r^2 \cdot k_1$. Of this light the amount $Is_1$ that is directed to the outlet window WOs is given as $$Is_1 = P \cdot r^2 \cdot k_1 \cdot r' \cdot k_2. \quad (6)$$

This amount corresponds to the amount $Ir_1$ of the reference light given as the equation (1). Dividing the amount Is by the amount Ir, we obtain the absolute reflectance r'.

Therefore, if the amount Ir is measured with the light measuring device positioned in front of the outlet window WOr and the amount Is is measured with the measuring device positioned in front of the outlet window WOs, the ratio between the two measured values will give the absolute reflectance r' of the sample.

As can be easily understood, in order to measure the two values it is necessary to move the measuring device between the two outlet windows WOr and WOs. This not only requires a troublesome operation but also makes the whole structure of the apparatus large in size so that it is very difficult to design the apparatus as an optional accessory for use in a spectrophotometer. If an individual light measuring device is provided in front of each of the two outlet windows, it would not be necessary to move the light measuring devices. However, there is no other means to compensate for inherent difference in sensitivity between the two measuring devices than to exchange the relative positions of the two devices, and exchanging their positions would make the provision of two measuring devices meaningless.

SUMMARY OF THE INVENTION

Accordingly, the object of the invention is to provide an apparatus for measuring the absolute reflectance of a sample, which employs an integrating sphere and in which the above-mentioned problem has been completely solved in a very simple manner.

In a preferred embodiment of the invention, the apparatus is provided with an integrating sphere formed with a single inlet window through which a beam of light from a monochromator is introduced into the sphere, a pair of outlet windows through which the light from inside the integrating sphere is taken out, and a sample window which is opposite to one of the outlet windows diametrically of the integrating sphere and in which a sample to be measured is set so as to be exposed inside the integrating sphere. The inlet window, the outlet windows and the sample window are provided in a single plane including the center of the integrating sphere. The apparatus is further provided with a light measuring device including a photodetector and disposed in front of one of the pair of outlet windows so that the photodetector receives the light emerging out of that one outlet window to produce a corresponding electrical signal, which expresses, say, the previously mentioned amount Ir of the reference light.

The light measuring device is held stationary while the integrating sphere is rotatable about an axis coinciding with a diametrical line in the previously mentioned single plane so that the other of the two outlet windows can be brought into alignment with the light measuring device, whereupon the photodetector receives the light coming out of that other outlet window to produce a corresponding electrical signal, which expresses, say, the previously mentioned amount Is of the sample light.

A signal processing circuit processes the above-mentioned two electrical signals to provide a ratio of Is/Ir, which expresses the absolute reflectance of the sample under measurement.

In another preferred embodiment of the invention, the positions of the light source and the light measuring device in the above-mentioned embodiment are exchanged so that the light from the source is introduced into the integrating sphere through one or the other of the outlet windows and the light emerges from the integrating sphere through the inlet window so as to be received by the light measuring device.

BRIEF DESCRIPTION OF THE DRAWING

FIG. 9 is an enlarged view, in vertical section, of a portion of the supporting frame shown in FIG. 8; and FIG. 10 is a side view, in partially vertical section, of the integrating sphere with a mechanism for rotating the same.

DESCRIPTION OF THE PREFERRED EMBODIMENTS

Figure 1:
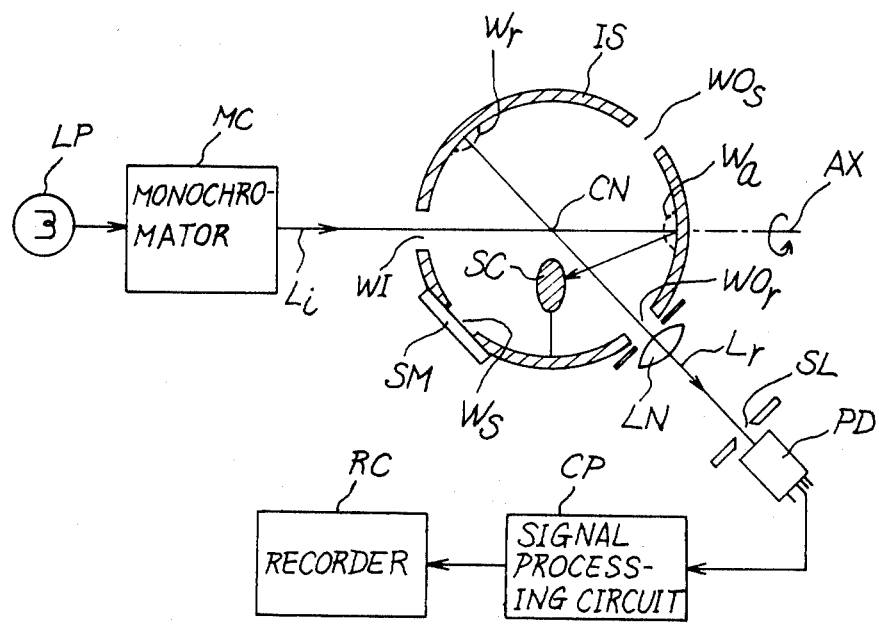
FIG. 1 is a schematic view of one embodiment of the invention.

Referring to FIG. 1, the structure of the apparatus has already been described hereinbefore with explanation of the principle of measurement of absolute reflectance. The inlet window WI, the outlet windows WOr and WOs and the sample window Ws are formed in a single plane including the center CN of the integrating sphere IS, and the integrating sphere is rotatable about its axis AX coinciding with a diametrical line lying in the above-mentioned single plane, so that the integrating sphere can be brought selectively into the symmetrical positions shown in FIGS. 1 and 2.

Figure 2:
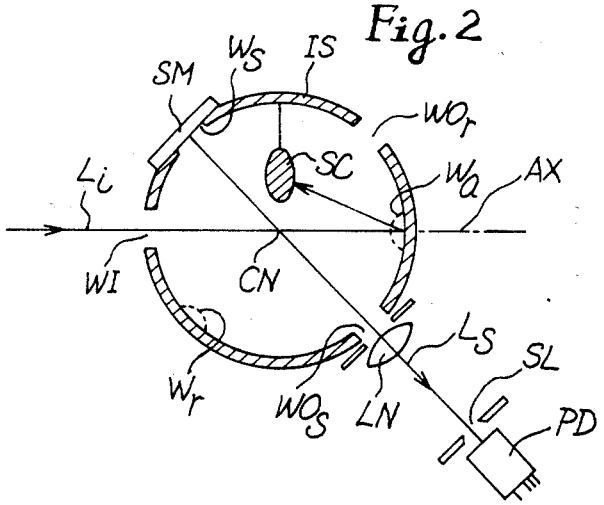
FIG. 2 is a view similar to FIG. 1 but showing the integrating sphere in a different operative position rotated 180° from the position in FIG. 1.

With the integrating sphere IS set in the position of FIG. 1, the total amount Ir of the light from the outlet window WOr is measured, and then the integrating sphere is rotated for 180° about the axis AX into the position of FIG. 2, where the total amount Is of the light from the outlet window WOs is measured. A signal processing circuit CP processes the outputs of the photodetector PD to provide a ratio of Is/Ir, which expresses the absolute reflectance r' of the sample. The data is recorded by a recorder RC.

In the arrangement of FIGS. 1 and 2 the sample SM is illuminated by diffuse light and the reflectance Rd/o in the direction perpendicular to the surface of the sample is measured.

Figure 3:
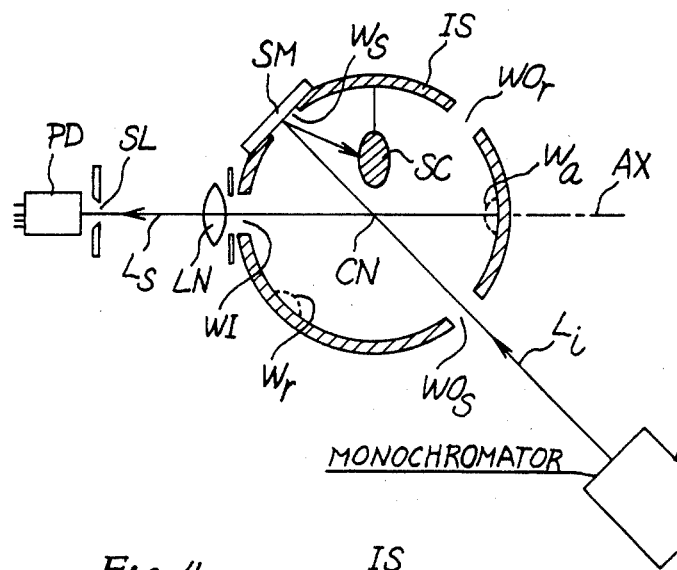
FIG. 3 is a schematic view of another embodiment of the invention.

It is possible to illuminate a sample directly with the light from the monochromator impinging perpendicularly onto the surface of the sample and obtain the reflectance Ro/d of the sample by measuring the diffuse light reflected by the sample surface. The arrangement of FIG. 3 is directed to the measurement of the reflectance Ro/d. In FIG. 3, the position of the light source (that is, the lamp LP and the monochromator MC) and that of the light measuring system (that is, the lens LN, the aperture AP and the photodetector PD) in FIGS. 1 and 2 are exchanged. In particular, the light from the monochromator is introduced into the integrating sphere IS through the outlet window WOs while the output light from the integrating sphere is taken out through the inlet window WI, so that the total amount Is of the output light is measured. When the integrating sphere IS is rotated to a symmetrical position not shown but corresponding to FIG. 1, the light from the monochromator is introduced into the integrating sphere through the other outlet window WOr and the output light from the integrating sphere is taken out through the inlet window WI, so that the total amount Ir of the output light is measured. In this second embodiment of the invention, from the ratio of the two measured values Is and Ir it is possible to obtain the absolute reflectance Ro/d of the sample as in the previous embodiment.

Figure 4:
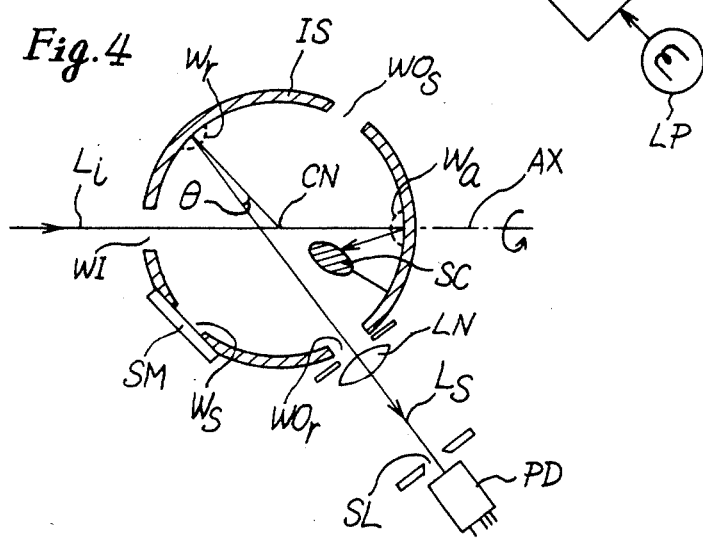
FIG. 4 is a schematic view of a third embodiment of the invention.
Figure 5:
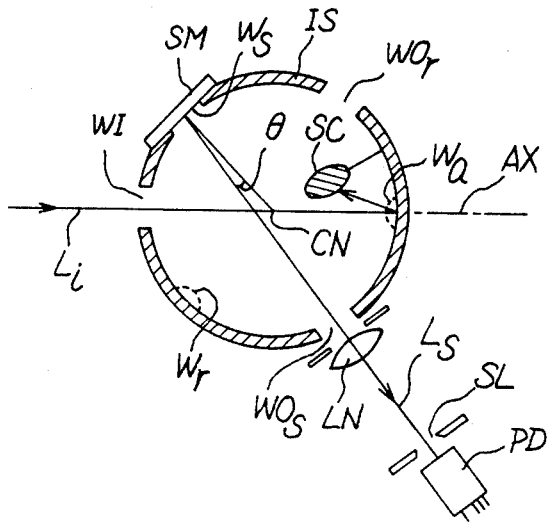
FIG. 5 is a view similar to FIG. 4 but showing the integrating sphere in a different operative position rotated 180° from the position in FIG. 4.

FIGS. 4 and 5 show a third embodiment of the invention, wherein the straight line connecting the center of the region Wr or the sample window Ws and that of the outlet window WOr or WOs (which line coincides with the optical axis of the light measuring device) does not pass the center CN of the integrating sphere IS, but makes an angle $\theta$ with the diametrical line passing the center of the region Wr or the window Ws. With this arrangement it is possible to measure the reflectance Rd/$\theta$ of the sample with respect to the light reflected obliquely from the sample surface illuminated by diffuse light.

Figure 6:
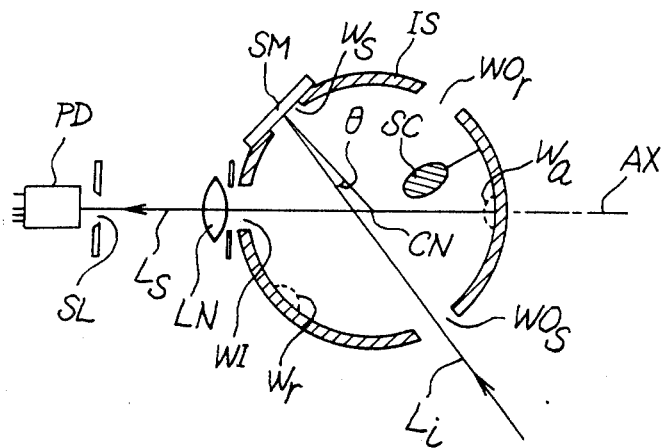
FIG. 6 is a schematic view of a fourth embodiment of the invention.

FIG. 6 shows a fourth embodiment of the invention, wherein the position of the light source (the lamp LP and the monochromator MC) and that of the light measuring device (the lens LN, the aperture AP and the photodetector PD) in FIGS. 4 and 5 are exchanged. With this arrangement it is possible to measure the reflectance R$\theta$/d of the sample with respect to the diffuse light reflected by the sample surface illuminated directly by the light from the monochromator impinging obliquely on the sample surface.

Figure 7:
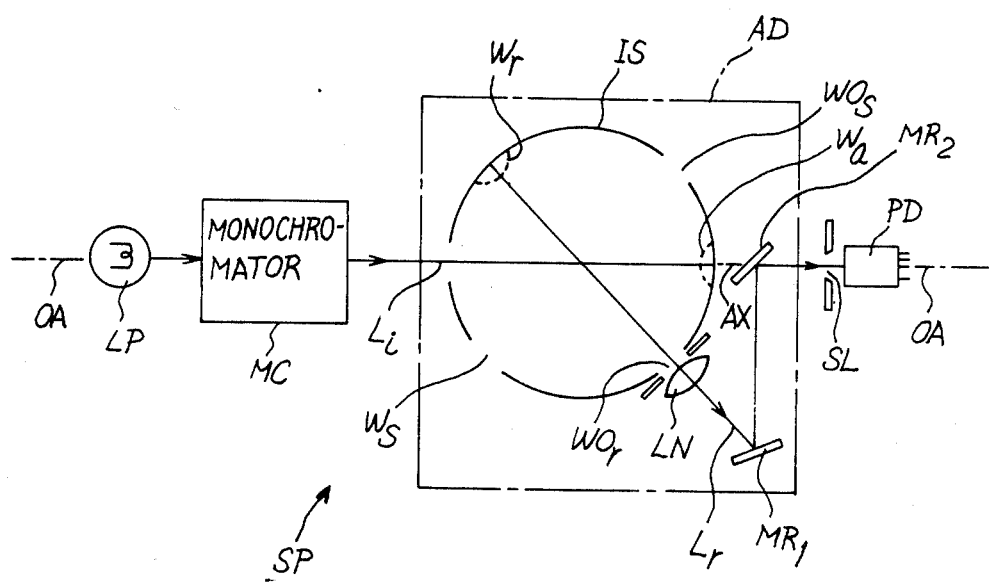
FIG. 7 is a schematic top plan view of the apparatus fitted as an optional accessory in a spectrophotometer.

FIG. 7 schematically shows a fifth embodiment of the invention, wherein the integrating sphere IS, the lens LN with a pair of plain mirrors MR$_1$ and MR$_2$ are assembled to form an optional accessory ACC for use in the sample chamber of an existing spectrophotometer SP. The mirrors MR$_1$ and MR$_2$ are so arranged as to bring the output light from the integrating sphere IS into coincidence with the optical axis OA of the spectrophotometer. The integrating sphere of the optional accessory ACC is rotatable about its axis AX just as in the previous embodiments.

Figure 8:
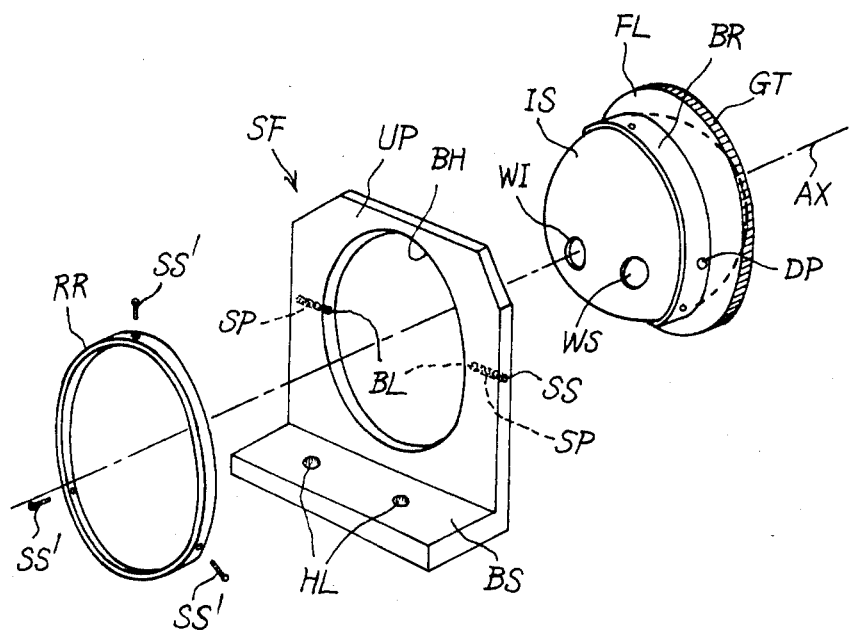
FIG. 8 is an exploded perspective view of the integrating sphere with a mechanism for rotatably supporting the integrating sphere.

FIGS. 8 to 10 show by way of example a mechanism for rotating the integrating sphere IS in the above-mentioned embodiments. A bearing ring BR is fixed to the integrating sphere IS and provided with an integral flange FL, the periphery of which is formed into a plurality of gear teeth GT, somewhat schematically shown in FIG. 8. A support frame SF comprises a base BS and an upstanding plate UP. The base BS is secured to a frame of, say, a spectrophotometer not shown by means of bolts not shown inserted into a pair of holes HL formed in the base. The upstanding plate UP is formed with a circular bearing hole BH the inner diameter of which is slightly larger than the outer diameter of the bearing ring BR.

A pair of through bores TB are formed in the upstanding plate UP of the support frame SF at diametrically opposite sides of the circular bearing hole BH and in alignment with each other. A stopper ball BL is provided in each of the through bores TB, and a compression spring SP held in each through bore TB by a set screw SS urges the ball BL to partially project on the inner circumferential surface of the bearing hole BH. A pair of dimples DP are formed on the outer circumferential surface of the bearing ring BR of the integrating sphere at the diametrically opposite sides thereof.

The bearing ring BR is inserted into the bearing hole BH in the support frame SF from one side of the upstanding plate UP thereof so that an axial end portion of the bearing ring BR opposite to the flange FL projects at the opposite side of the upstanding plate UP of the support frame SF. A retainer ring RR is fitted on and fixed to the projecting axial end portion of the bearing ring BR by means of set screws SS', so that the integrating sphere IS is held in the bearing hole BH of the support frame SF so as to be rotatable about its axis AX which passes the center of the bearing hole BH, with the bearing hole BH rotatably supporting the bearing ring BR together with the integrating sphere IS.

The stopper balls BL on the inner circumferential surface of the bearing hole BH engage in the dimples DP on the outer circumferential surface of the bearing ring BR at such a rotational position of the integrating sphere IS relative to the support SF that the output light from the integrating sphere through the outlet window WOr or WOs enters the photodetector PD.

For rotation of the integrating sphere IS about its axis AX, a drive pinion PN meshes with the external gear teeth GT of the flange FL of the bearing ring BR. The pinion PN is driven by a motor MO to drive the external gear teeth GT and consequently the integrating sphere IS about its axis AX. A controller CL provides control signals for the motor MO.

The invention has the following advantages: since it is not necessary to change the position of the light measuring device, the operation of measuring is simple; since the light measuring device does not occupy two positions for operation, a smaller space than was required in the prior art instruments suffices for installation; since the integrating sphere has only to be supported rotatably, the mechanism is simple; and since the device can be applied as an optional accessory to an existing spectrophotometer, it is possible to measure the absolute reflectance of a sample with ease and at a low cost.

What I claim is:

1. Apparatus for measuring the absolute reflectance of a sample, comprising:
   (a) an integrating sphere provided in a spherical wall thereof with four windows having a center of each window lying in a single plane including a center of said sphere, a first one of said four windows having its center coinciding with a diametric line included in said plane while a second and a third one of said four windows are arranged symmetrically with respect to said diametric line, with a fourth one of said windows having a sample set therein so as to face inwardly of said integrating sphere;
   (b) a light source so arranged as to introduce a beam of light into said integrating sphere;
   (c) light intercepting means provided in said integrating sphere and arranged in a partial light intercepting relation to said sample so as to prevent diffuse light which is reflected a first time by an inner surface of said sphere from directly impinging on said sample and to allow light reflected by said inner surface said first time to impinge directly on said inner surface so as to be reflected a second time and to directly exit said sphere through one of said second and third windows;
   (d) light measuring means so arranged as to receive light emerging from inside said integrating sphere;
   (e) means for rotating said integrating sphere about an axis coinciding with said diametric line so that said integrating sphere selectively takes first and second positions 180° apart from each other thereby to change the operative position of said second and third windows relative to said light source and said light measuring means; and
   (f) means for processing measured data obtained by said measuring means when said integrating sphere is at said first and second positions, respectively, thereby to obtain the absolute reflectance of said sample.

2. The apparatus of claim 1, wherein said light source is positioned so that light from said light source enters said integrating sphere through said first window and said light measuring means is positioned so as to receive light emerging from inside said integrating sphere through said second window when said integrating sphere is at said first position and alternatively through said third window when said integrating sphere is at said second position.

3. The apparatus of claim 1, wherein said light source is positioned so that light from said light source enters said integrating sphere through said second window when said integrating sphere is at said first position and alternatively through said third window when said integrating sphere is at said second position, and said light measuring means is so positioned as to receive light from inside said integrating sphere through said first window.

4. The apparatus of claim 2 or 3, wherein said fourth window is positioned symmetrically with one of said second and third windows with respect to said center of said integrating sphere.

5. The apparatus of claim 2 or 3, wherein said fourth window is so positioned that a straight line connecting the center of said fourth window and the center of that one of said second and third windows which is on the side of said axis opposite to said fourth window does not pass the center of said integrating sphere.

6. The apparatus of claim 1, wherein said rotating means comprises a frame for supporting said integrating sphere for rotation about said axis, a ring gear fixed to said integrating sphere and having external gear teeth, a pinion gear meshing with said ring gear, drive means for rotating said pinion gear and means for controlling the operation of said drive means.

* * * * *